US008987324B2

(12) United States Patent
Bourdy et al.

(10) Patent No.: US 8,987,324 B2
(45) Date of Patent: Mar. 24, 2015

(54) USE OF SIMALIKALACTONE E AS AN ANTICANCER AGENT (75) Inventors: Geneviève Bourdy, Ramonville Saint Agne (FR); Patrick Auberger, Nice (FR); Valérie Jullian, Toulouse (FR); Guillaume Robert, Nice (FR); Eric Deharo, Auterive (FR)

(73) Assignee: Institut de Recherche pour le Developpement, Marseilles (FR)

( * ) Notice: Subject to any disclaimer, the term of this patent is extended or adjusted under 35 U.S.C. 154(b) by 0 days.

(21) Appl. No.: 13/979,647

(22) PCT Filed: Jan. 13, 2012

(86) PCT No.: PCT/IB2012/050179
§ 371 (c)(1),
(2), (4) Date: Sep. 24, 2013

(87) PCT Pub. No.: WO2012/095820
PCT Pub. Date: Jul. 19, 2012

(65) Prior Publication Data
US 2014/0011868 A1    Jan. 9, 2014

(30) Foreign Application Priority Data
Jan. 14, 2011   (FR) ..................................... 11 00125

(51) Int. Cl.
*A61K 31/366*    (2006.01)
*A61K 45/06*     (2006.01)

(52) U.S. Cl.
CPC ............... *A61K 31/366* (2013.01); *A61K 45/06* (2013.01)
USPC ...................................................... 514/453

(58) Field of Classification Search
USPC ........................................................ 514/453
See application file for complete search history.

(56) References Cited

U.S. PATENT DOCUMENTS 5,605,810 A    2/1997   Morre et al.

FOREIGN PATENT DOCUMENTS

FR        2 946 980         12/2010
WO    2010146257 A8        12/2010

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Cachet et al., Antimalarial Activity of Simalikalactone E, a New Quassinoid from *Quassia Amara* L. (Simaroubaceae), Antimicrobial Agents and Chemotherapy, 53, pp. 4393-4398, 2009.
*Quassia* Tincture from Amazon Herbs, Tropilab Inc., http://web.archive.org/web/20090309071437/http://www.tropilab.com/quassiatincture.htm, retrieved Jun. 29, 2011.
Muhammad et al., A New Antimalarial Quassinoid from *Simaba orinocensis*, Journal of Natural Products, 67, pp. 772-777, 2004.
Kumar et al., Synthetic Medicinal Chemistry of Selected Antimalarial Natural Products, Bioorganic & Medicinal Chemistry, 17, pp. 2236-2275, 2009.
Fukamiya et al., Structure-Activity Relationships of Quassinoids for Eukaryotic Protein Synthesis, Cancer Letters, 220, pp. 37-48, 2005.
Murakami et al., Multidrug-Resistant Cancer Cell Susceptibility to Cytotoxic Quassinoids, and Cancer Chemopreventive Effects of Quassinoids and Canthin Alkaloids, Bioorganic & Medicinal Chemistry, 12, pp. 4963-4968, 2004.
Trager et al., Antimalarial Activity of Quassinoids Against Chloroquine-Resistant *Plasmodium falciparum* in Vitro, The American Journal of Tropical Medicine and Hygiene, 30, pp. 531-537, 1981.

* cited by examiner

*Primary Examiner* — Kristin Vajda
(74) *Attorney, Agent, or Firm* — Morgan, Lewis & Bockius LLP (57) ABSTRACT The invention relates to Simalikalactone E (SkE) to be used for preventing and/or treating cancers.

14 Claims, 8 Drawing Sheets

USE OF SIMALIKALACTONE E AS AN ANTICANCER AGENT

The subject of the invention is the use of Simalikalactone E (SkE) as an anticancer agent, more particularly for preventing and/or treating epithelial and hematological cancers.

Simalikalactone E is a quassinoid isolated from an Amazonian plant of the family Simaroubaceae, i.e. the *Quassia amara* plant renowned for its antiparasitic efficacy and its low toxicity (Vigneron et al., Journal of Ethnopharmacology (2005), Vol. 98, pp. 351-360; Bertani et al., Journal of Ethnopharmacology (2005), Vol. 98, pp. 45-54). Simalikalactone E has been described in patent application FR No. 09 02959 for its antimalarial activity in vitro against *Plasmodium falciparum*, in vivo orally against murine *Plasmodium*, and also against the hepatocyte and gametocyte forms of this same parasite in humans. It has been demonstrated that Simalikalactone E inhibits 50% of the growth of *Plasmodium falciparum* in culture at doses of between 24 and 68 nM, independently of the chloroquine sensitivity of the strain tested. It inhibits 50% of the growth of Vero mammalian cells at a dose of 6574 nM, which gives it a selectivity index greater than 100. Simalikalactone E also reduces the gametocyte level by 50% at a concentration seven times lower than that obtained with primaquine, the reference molecule for this activity. In vivo, on a murine model of malaria, Simalikalactone E inhibits 50% of the growth of *Plasmodium vinckei petteri* at doses of 0.5 and 1 mg/kg/day intraperitoneally and orally, respectively (chloroquine, the reference molecule, inhibits 50% of the growth of *Plasmodium vinckei petteri* at a dose of 3 mg/kg/day intraperitoneally).

A preclinical study in mice has subsequently made it possible to identify the doses of Simalikalactone E tolerated: 1 mg/kg/d orally for 4 days in the Peters four-day suppressive antimalarial test (Cachet et al., Antimicrobial Agents Chemotherapy (2009) Vol. 53, No. 10, pp. 4393-4398). This study has also demonstrated a moderate cytotoxic action of Simalikalactone E on certain cell lines. However, no mention is made of any antitumor effect of Simalikalactone E in vitro or in vivo. Furthermore, it should also be noted that the demonstration of a cytotoxic activity of a given compound even with respect to tumor cell lines does not in any way imply an anticancer effect, this compound possibly proving to be inactive in vivo or else to exhibit cytotoxicity incompatible with its administration to a living being.

Surprisingly, the inventors have been able to note that Simalikalactone E proves to be a selective inhibitor of the Ras/Raf/MEK/Erk signaling pathway, a signaling pathway frequently modified in cancers.

The Ras/Raf/MEK/Erk signaling pathway is activated in 20% of known cancers, i.e. breast, prostate, pancreatic, lung and thyroid cancers, and in more than 50% of cases of acute leukemia. For example, the Ras molecule is mutated in 15% of human cancers, and more particularly N-ras (Q61L) is mutated in 15 to 30% of melanomas and B-raf in 60% of melanomas and in 30 to 50% of thyroid cancers.

Activation of the Ras/Raf/MEK/Erk signaling pathway is rapidly and clearly identifiable. One of the methods which can be used to identify this pathway is the analysis of protein phosphorylation via a flow cytometry or "phosphoflow" technique (Firaguay et al., Analysis of signaling events by dynamic phosphoflow cytometry. Sci Signal, 2: p. 13, 2009). This technique makes it possible to dynamically monitor the level of phosphorylation, and therefore the activation of the MEK and Erk kinases.

Furthermore, well-defined mutations or translocations are associated with pathological conditions in which the Erk1/2 (MAP kinase) pathway is superactivated. These known mutations can be rapidly identified in a patient by pyrosequencing (Borras et al., BMC Cancer 2001, 11: 406, Lennerz et al., Br. J. Haematol., 7 Dec. 2011, DOI: 10.1111/j.1365-2141.2011.08963.x), a technique for carrying out rapid sequencing without cloning, with direct reading of the sequence obtained, at a lower cost than sequencing using the Sanger method.

As a result, Simalikalactone E has a more marked effect in cancer cell lines in which these pathways are constitutively activated, such as melanoma lines and malignant hemopathies.

The inventors have established that Simalikalactone E has powerful antiproliferative and cell-death inducing effects in vitro, more particularly on tumor cells in which the Erk1/2 (MAP kinase) pathway is superactivated. The mechanism of action identified is linked to an inhibition of the Ras/Raf/MEK/Erk signaling pathway. The targeting of the Erk1/2 (MAP kinase) pathway is a major challenge in cancerology, since activating mutations or superactivations of this pathway are commonly found in human cancers. This is in particular the case for B-raf in melanoma, which results in a superactivation of the Erk1/2 kinase (MAP kinase).

Likewise, in chronic myeloid leukemia (CML), the p210 BCR-ABL tyrosine kinase encoded by the gene resulting from the translocation t(9;22), an abnormality responsible for the disease, induces a superactivation of the Erk1/2 kinase (MAP kinase). Moreover, certain CML lines resistant to TKIs (Glivec®, Sprycel®) exhibit an exacerbation of the Erk1/2 kinase (MAP kinase) due to an increase in the expression and in the activity of the Src kinases, Fyn and Lyn (Fenouille et al., Cancer Research (2010), 70 (23): 9659-70; Gioia et al., Blood, 2011, 118: 2211-2221).

The subject of the invention is therefore Simalikalactone E corresponding to formula 1 below:

SkE with, as indication, the prevention and/or treatment of cancers, and more particularly epithelial and hematological cancers, Simalikalactone E effectively inhibiting the Erk1/2 (MAP kinase) pathway, and more particularly the phosphorylation of the Raf kinase and the downstream kinases MEK and Erk.

The subject of the invention is thus Simalikalactone E with, as indication, the prevention and/or treatment of epithelial cancers chosen from melanomas, breast, prostate, ovarian, kidney, intestinal, colon, pancreatic, lung and thyroid cancers and ENT cancers.

The subject of the invention is also Simalikalactone E with, as indication, the prevention and/or treatment of hematological cancers chosen from malignant hemopathies, and more particularly myeloproliferative syndromes (MPS), including chronic myeloid leukemia (CML), myelodysplastic syndromes (MDS), multiple myeloma (MM), acute myeloid leukemias (AML) and acute lymphoblastic leukemias (ALL), the use of Simalikalactone E being more particularly suitable for preventing and/or treating chronic myeloid leukemia (CML), myelodysplastic syndromes (MDS), multiple myeloma (MM) and acute lymphoblastic leukemias (ALL).

The appropriate administration forms include the forms that are administrable orally, such as tablets, soft or hard gel capsules, powders, granules and oral solutions or suspensions, topically, for example in the form of creams, gels, ointments or lotions, intravenously, subcutaneously, intramuscularly, in the form of a suppository, of an eye lotion, of an ophthalmic gel or of a delayed-release implant under the skin.

It is possible to prepare a solid composition in tablet form by mixing the active ingredient, Simalikalactone E, with one or more pharmaceutically acceptable excipients, such as, for example, gelatin, starch, lactose, magnesium stearate, talc, silica, gum arabic, mannitol, microcrystalline cellulose, hydroxypropyl-methylcellulose, or analogous components. The tablets can be coated with sucrose, with a cellulose-based derivative or with other materials suitable for coating. The tablets can be prepared by various techniques well known to those skilled in the art, such as direct compression, dry granulation, wet granulation or the hotmelt process.

It is also possible to prepare a composition in gel capsule form by mixing the active ingredients with a diluent and by pouring the mixture obtained into soft or hard gel capsules.

The daily doses of Simalikalactone E are advantageously the following: from 10 to 50 mg/kg/d of Simalikalactone E. In particular, these doses are suitable for oral administration.

There may be particular cases where higher or lower dosages are appropriate; such dosages do not depart from the scope of the invention. According to the usual practice, the dosage appropriate for each patient is determined by the physician according to the mode of administration and the weight and response of said patient to the treatment.

The medicament of the invention is intended to be administered for preferentially 1 to 60 consecutive days, and preferably from 20 to 40 days, in one or more daily intakes, preferably in a single intake per day.

The present invention also relates to a pharmaceutical composition comprising Simalikalactone E as active ingredient in combination with another anticancer active ingredient, and at least one pharmaceutically acceptable excipient. The anticancer active ingredients combined with Simalikalactone E are chosen from the active ingredients known to those skilled in the art according to the anticancer disease to be treated.

Simalikalactone E can be isolated from mature leaves of Quassia amara by employing a protocol which comprises the following steps: the mature leaves of Quassia amara are ground and extracted with methanol. This extract is dissolved in a two-phase system based on n-heptane, ethyl acetate, methanol and water. The lower phase is collected and its volume is reduced by half by evaporation under reduced pressure. This solution is extracted with ethyl acetate. The ethyl acetate is evaporated off. The residue obtained is dissolved in chloroform and washed with a slightly basic aqueous solution. The organic phase is collected, dried and concentrated under reduced pressure. This extract is dissolved in ethyl acetate and washed with water. The organic phase is evaporated under reduced pressure and the residue obtained is eluted with ethyl acetate through a silica column.

The extract obtained is purified according to the following protocol: the extract is fractionated by centrifugal partition chromatography using an Arizona H system composed of n-heptane, ethyl acetate, methanol and water, in ascending mode. 25 ml samples are collected. The samples comprising Simalikalactone E are combined and purified by silica column chromatography, elution being carried out with cyclohexane/ethyl acetate mixtures of increasing polarity. Simalikalactone E is eluted with the 50/50 cyclohexane/ethyl acetate mixture.

In addition to the above arrangements, the invention also comprises other arrangements which will emerge from the further description which follows, which refers to examples demonstrating the antitumor properties of Simalikalactone E, and also to the appended drawings in which:

FIGS. 7 and 8 show the effect of Simalikalactone E on xenografts of K562-Luc cells in Nude mice (FIG. 7: absolute quantification of the number of photons emitted in absolute value (cpm=counts per minute) for PBS (phosphate buffered saline), Ima (imatinib 60 mg/kg) and SkE (Simalikalactone E 1 mg/kg); FIG. 8: acquisition carried out by virtue of a Biospace photoimager with a 5 min acquisition (A: mice treated with PBS, B: mice treated with 60 mg/kg of imatinib and C: mice treated with 1 mg/kg of SkE)).

EXPERIMENTAL SECTION

A—Protocol for Obtaining Simalikalactone E

Quassia amara leaves were harvested at Rémire-Montjoly in French Guiana. A specimen (GB3012) was harvested and the botanical identification thereof was confirmed at the Cayenne Herbarium in Guiana.

Simalikalactone E was isolated from Quassia amara by using the following protocol: 1 kg of dried mature leaves of Quassia amara are ground and extracted for 24 hours with 6 l of methanol, this being carried out twice, to give 200 g of extract. 50 g of this extract are dissolved in 2 l of a two-phase system composed of n-heptane, ethyl acetate, methanol and water in the proportions 3/2/3/2. The heaviest phase is concentrated to 500 ml, and 500 ml of water are added thereto. This solution is extracted with 1 l of ethyl acetate. The ethyl acetate is evaporated off under reduced pressure. The residue obtained is dissolved in 1.5 l of chloroform and washed four times with a 0.001M sodium hydroxide solution. The organic phase is collected, dried over anhydrous magnesium sulfate and concentrated under reduced pressure, to give 3.3 g of extract. This extract is dissolved in 500 ml of ethyl acetate and washed with 500 ml of water. The organic phase is evaporated under reduced pressure and the residue obtained is eluted rapidly with ethyl acetate through a short silica column. After the ethyl acetate has been evaporated off, 1.0 g of extract is obtained. This extract is fractionated by centrifugal partition chromatography (Kromaton apparatus, equipped with a 1 l rotor), using an Arizona H system composed of n-heptane, ethyl acetate, methanol and water in the proportions 1/3/1/3, in ascending mode, at a temperature of 16° C. The flow of solvent is 25 ml/min, the rotor speed is 1000 rpm and is changed during the elution so as to maintain a pressure of 40 bar. The extract (1.0 g) is dissolved in 40 ml of Arizona H system, filtered and injected. Samples of 25 ml are collected. The samples are combined to give the fraction F1 (120 mg). This fraction is purified by silica column chromatography, elution being carried out with cyclohexane/ethyl acetate mixtures of increasing polarity. Simalikalactone E (10 mg) is eluted with the 50/50 cyclohexane/ethyl acetate mixture. The yield from the plant is 0.004%.

The Simalikalactone E was characterized by mass spectrometry, by NMR and infrared spectroscopy, and via its optical rotation. Since crystals were obtained from deuterated methanol, an X-ray image of the molecule was also obtained. Its physicochemical characteristics are the following:

APCIMS, 579 (MH$^+$), 561 (MH$^+$-H$_2$O).

$^1$H NMR (CDCl$_3$, 500 MHz), δ 6.19 (m, 1H, H-15), 6.17 (s, 1H, H-3), 5.19 (dd, J=2.6, 11.7 Hz, 1H, H-6), 4.75 (d, J=5.1 Hz, 1H, H-11), 4.70 (d, J=2.6 Hz, 1H, H-7), 4.65 (d, J=7.4 Hz, 1H, H-17a), 4.19 (s, 1H, H-1), 3.83 (s, 1H, H-12), 3.70 (d, J=7.4 Hz, 1H, H-17b), 3.37 (d, J=11.5 Hz, 1H, H-5), 2.51 (m, 1H, H-24), 2.48 (m, 1H, H-19), 2.45 (m, 1H, H-14), 2.43 (m, 1H, H-9), 2.08 (s, 3H, H-30), 1.79 (m, 2H, H-21a, H-26a), 1.61 (m, 1H, H-26b), 1.53 (m, 1H, H-21b), 1.45 (s, 3H, H-28), 1.35 (s, 3H, H-29), 1.21 (d, J=7.0 Hz, 3H, H-20), 1.19 (d, J=7.0 Hz, 3H, H-25), 1.01 (t, J=7.4 Hz, 3H, H-22), 0.99 (t, J=7.4 Hz, 3H, H-27).

$^{13}$C NMR (CDCl$_3$, 125 MHz), δ 196.5 (C-2), 176.2 (C-23), 175.2 (C-18), 166.5 (C-16), 163.0 (C-4), 126.5 (C-3), 82.8 (C-7), 81.8 (C-1), 80.0 (C-13), 79.8 (C-12), 74.2 (C-11), 70.9 (C-17), 69.1 (C-6), 67.3 (C-15), 52.7 (C-14), 50.4 (C-10), 46.1 (C-8), 45.9 (C-5), 41.3 (C-24), 41.3 (C-19), 41.1 (C-9), 27.2 (C-26), 26.7 (C-21), 26.1 (C-30), 22.8 (C-28), 16.7 (C-20), 15.6 (C-25), 12.5 (C-29), 11.7 (C-22), 11.5 (C-27).

IR (KBr, cm$^{-1}$): 2965, 2926, 2855, 1766, 1738, 1722, 1667.

$[\alpha]_D^{26}$=+94° (c=0.35, CHCl$_3$).

B—Biological Activity

B1—Materials and Methods

The drugs used are diluted beforehand 1000-fold in pure DMSO (final concentration of DMSO: 0.1%).

B1-1. XTT Cell Viability Measurement

This test measures the activity of mitochondrial succinate dehydrogenase, which represents an index of cell viability. This enzyme converts XTT into orange formazan. On day 0, the K562-Ima-S (sensitive to Ima), K562-Ima-R (resistant to Ima), A375 or MeWo cells are seeded at 15 000 cells/well (100 µl) in 96-well microplates and stimulated with increasing concentrations of Simalikalactone E [50-500 nM]. After 24 or 48 hours, 50 µl of tetrazolium (XTT reagent) are added to each well and the optical density at 490 nm is read every 30 minutes for 2 to 4 hours. The values obtained, which are an index of mitochondrial metabolism, make it possible to evaluate the percentage of live cells. Each condition is systematically carried out in triplicate.

B1-2. Evaluation of the Clonogenic Capacity of K562 Cells

Aliquots of methylcellulose (40% Methocult®, 1% L-glutamine, 5% FCS (fetal calf serum) and 54% IMDM (Iscove's modified Dulbecco's medium)) are heated for 1 h at 37° C. 400 µl of RPMI (Roswell Park Memorial Institute medium), 5% of FCS containing the treatment (1 µM imatinib, 100, 250 or 500 nM SkE), and then 10$^3$ K562 cells in 200 µl of medium are added to each aliquot. For each condition, 500 µl of the suspension obtained are then deposited in 3 wells of a 24-well plate. A nontreated condition serves as a control. The plates are incubated at 37° C. for 7 to 10 days. 75 µl of MTT tetrazolium salt (Roche) (2.5 mg/ml) are added to each well. The MTT tetrazolium salt is cleaved into purple-colored formazan crystals by the metabolically active cells. After incubation for 4 h at 37° C., the wells are photographed and the clones are quantified using the Image J program.

B1-3. Cell Death Measurement

The characterization of the type of cell death involved in the effect of Simalikalactone E is carried out according to the following protocols:

apoptosis (type I cell death) is studied by assaying caspase activity, caspases being cysteine proteases involved in this type of process. The apoptosis is also quantified by annexin V/propidium iodide co-labeling, the cells which externalize the annexin V at the level of their mitochondria being cells undergoing apoptosis, autophagic death (type II cell death) is analyzed by assaying cathepsin activity, these proteases being, for their part, involved in the degradation of the intracellular material included in vesicles (autophagolysosomes). Type II cell death can also be demonstrated by electron microscopy imaging, and western blots (protein transfers) are finally carried out using antibodies specific for the induction of apoptosis (cleavage of PARP and caspases) or of autophagic death (conversion of LC3-I into LC3-II and activation of cathepsins).

B1-4. Xenografts of K562-Luc Cells on Nude Mice

The line used for the xenografts is a K562-Luc line stably expressing the gene encoding luciferase. It is cultured in an RPMI 1640 medium containing 5% of FCS, supplemented with sodium pyruvate and with penicillin/streptomycin and containing 10 µM of blasticidin (antibiotic allowing the selection of the cells possessing the plasmid encoding luciferase).

For each injection, 10$^6$ K562-Luc cells are prepared in 200 µl of medium, 70% PBS and 30% matrigel. Each Nude mouse receives 1 subcutaneous injection on each flank. The mice receive a 100 µl intraperitoneal injection 3 times a week. Depending on the groups, the animals receive either PBS, or imatinib (60 mg/kg), or SkE (1 mg/kg).

The evaluation of tumor growth is carried out once a week.

Each animal, while awake, receives an injection of 100 µl of luciferin at 30 mg/ml (Calliper LifeSciences). After 5 min, the animals are anesthetized by inhalation of 5% isoflurane per minute and per liter of O$_2$. The animals are then transferred in groups of 5 into the photon imager where the anesthesia is maintained with 2% isoflurane. The luciferin is degraded by the luciferase expressed by the tumor cells. This degradation is accompanied by the emission of photons measured by the photon imager.

The size and the metabolic activity of the tumor can be evaluated by virtue of the intensity of the photon emission.

B2—Results

Figure 1:
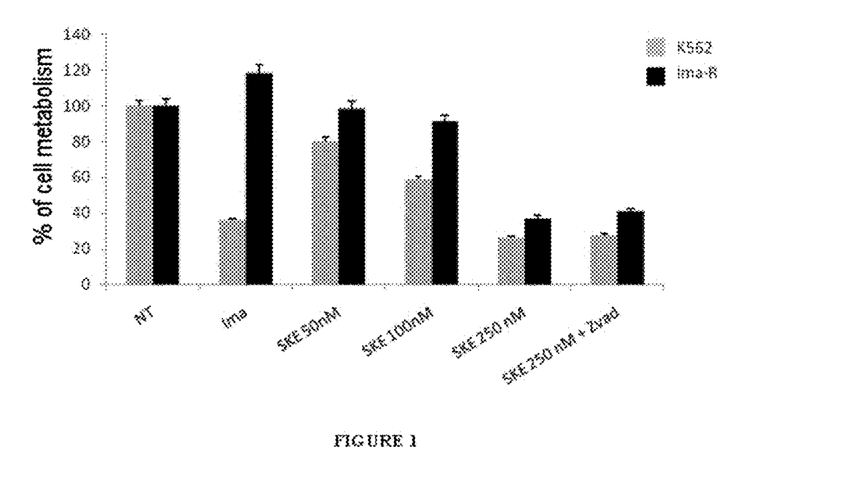
FIG. 1 represents the effect of Simalikalactone E on the growth and viability of K562-Ima-S and K562-Ima-R leukemia cell lines.

B2-1. Inhibition of the Growth and Reduction of the Viability of Various Tumor Cell Lines The K562-Ima-S and K562-Ima-R tumor lines are incubated for 48 hours with increasing concentrations of Simalikalactone E (0, 100 or 250 nM) in the absence or in the presence of a maximally effective concentration (50 µM) of z-Vad-fmk (Zvad), which is a pan-caspase inhibitor (apoptosis inhibitor).

The results are presented in FIG. 1.

The two leukemia lines are sensitive to the effect of Simalikalactone E, and the effect of Simalikalactone E is not modified in the presence of the caspase inhibitor, thereby demonstrating that the loss of viability of the cells in the presence of Simalikalactone E does not require apoptosis.

Figure 2:
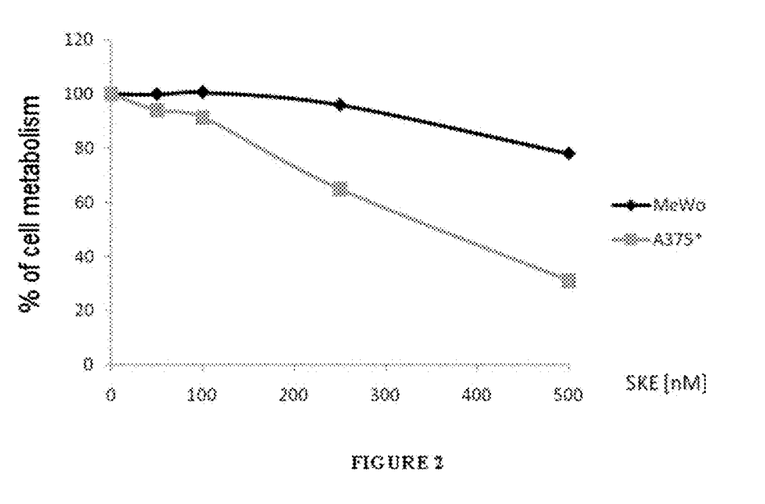
FIG. 2 represents the effect of Simalikalactone E on the growth and viability of A375 and MeWo melanoma cells, FIG. 3 demonstrates the effect of SkE on the clonogenic capacity of K562 cells (photographs taken with a Canon® digital apparatus)

A375 and MeWo melanoma cells are then treated in the presence of increasing doses of Simalikalactone E. 48 hours later, the cells are subjected to an XTT test. The A375 cells carry the V600E mutation on the B-raf oncogene, which is reflected by constitutive activation of the Erk pathway. Interestingly, the A375 cells are much more sensitive to Simalikalactone E than the MeWo cells, which do not have the B-raf mutation.

The results are presented in FIG. 2.

Figure 3:
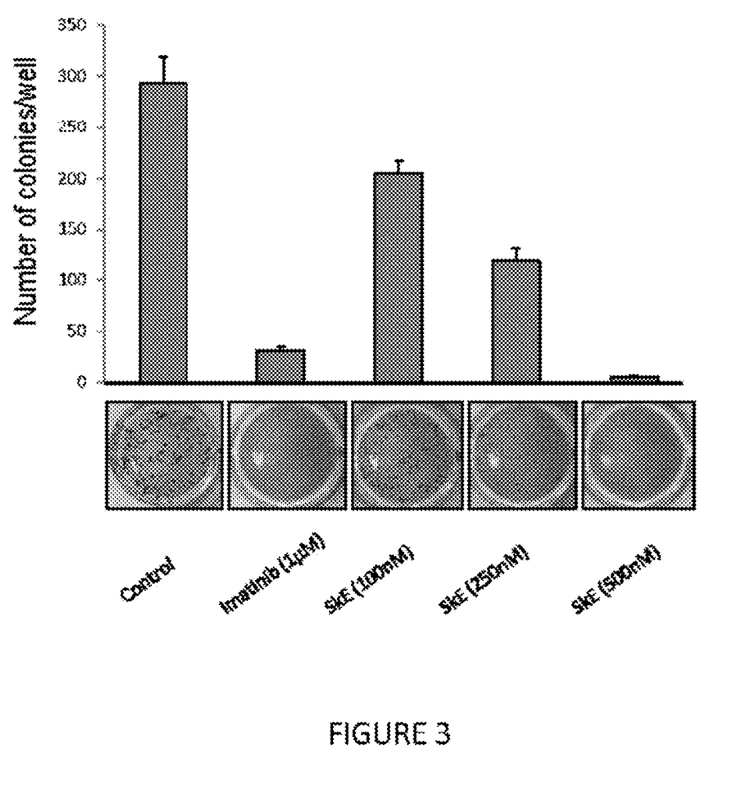

The effect of SkE on the clonogenic capacity of K562 cells has also been demonstrated in FIG. 3. The clonogenic capacity represents the capacity to form a colony from an isolated cell, which is a property inherent in cancer cells. It is thus observed that SkE is capable of inhibiting the clonogenic capacity of K562 cells as effectively as imatinib (reference treatment for the pathological condition CML) which acts directly on the chimeric protein BCR-ABL, at concentrations which are 2 to 4 times lower.

Figure 4:
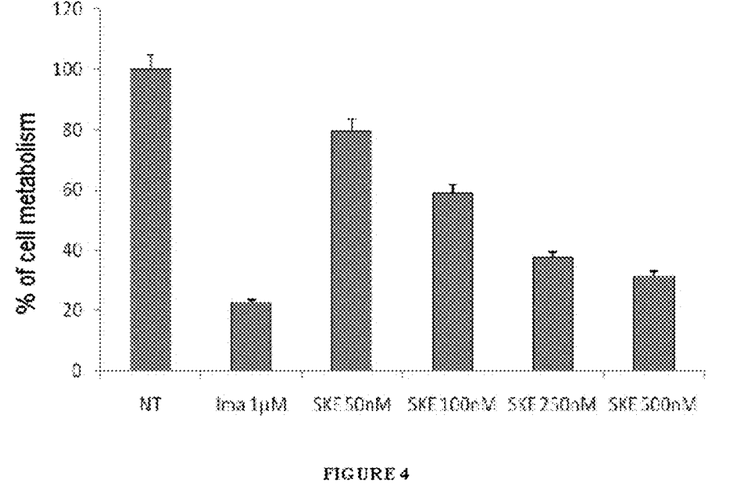
FIG. 4 represents the effect of Simalikalactone E on the viability of CD34+ human primary cells from patients suffering from CML.

B2-2. Inhibition of the Viability of CD34+Human Primary Cells from Patients Suffering from CML The primary cells from patients suffering from CML (purified CD34+Bcr-Abl+) are incubated in the presence of variable concentrations of Simalikalactone E for 48 hours, and then the cell viability is quantified using an XTT colorimetric test. Imatinib (Ima) is used as a positive control for the induction of death of the Bcr-Abl+ cells.

The results are presented in FIG. 4.

Simalikalactone E at a concentration of 500 nM proves to be as effective as imatinib for inhibiting the cell metabolism. The half-maximum effect is obtained for a dose of 100 nM of Simalikalactone E.

B2-3. Inhibition of Erk1/2 Kinase (MAP Kinase) Phosphorylation

Figure 5:
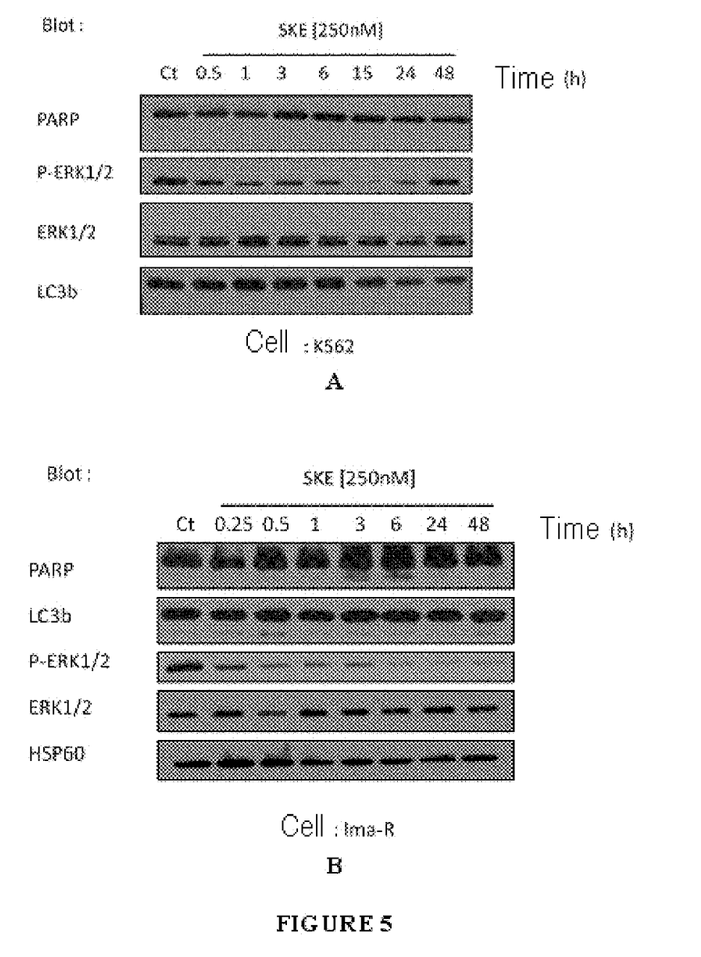
FIG. 5 shows the kinetic effect of Simalikalactone E on the markers of the various types of death: apoptotic death (PARP cleavage) and autophagic death (LC3 conversion). The level of phosphorylation of the Erk1/2 kinase (MAP kinase) is also observed.

The K562-Ima-S (A) and K562-Ima-R (B) cells are treated for variable periods of time with 250 nM of Simalikalactone E. The cells are then lyzed and protein extracts are prepared for western blot analysis. Finally, the membranes are incubated in the presence of the various anti-PARP, LC3b, p-Erk1/2, Erk1/2 and HSP60 antibodies. FIG. 5 shows that Simalikalactone E inhibits Erk1/2 kinase (MAP kinase) phosphorylation both in the imatinib-sensitive cells and in the imatinib-resistant cells, without modifying the overall expression of the Erk protein. This effect of Simalikalactone E occurs in the absence of apoptosis (no cleavage of PARP) and of autophagy (no modification of LC3).

Figure 6:
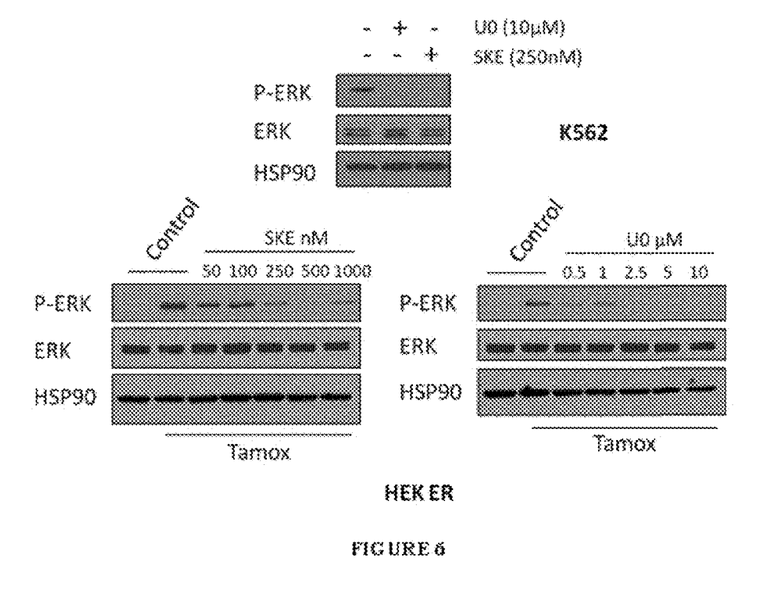
FIG. 6 shows the effect of Simalikalactone E on the phosphorylation of the Erk1/2 kinase (MAP kinase)

K562-Ima-S cells are then treated for 1 hour in the presence of 250 nM of Simalikalactone E or 10 μM of U0126 (specific inhibitor of MEK1/2, the kinase responsible for Erk1/2 (MAP kinase) phosphorylation and activation). The cells are then lyzed and protein extracts are prepared for western blot analysis. The membranes are then incubated in the presence of the p-Erk1/2, Erk1/2 and HSP60 antibodies. FIG. 6A shows that Simalikalactone E at a concentration of 250 nM is as effective as U0126 at a concentration which is 40 times higher, U0126 being the MEK1/2 inhibitor currently the most widely used for blocking the activity of Erk1/2 (MAP kinase) in vitro.

In the experiment presented in FIG. 6B, inducible HEK-Rafl-ER cells were used. These cells express the Raf kinase under the control of the estrogen receptor. The expression of Raf can therefore be induced in the presence of tamoxifen. The cells are preincubated for 30 minutes with increasing doses of Simalikalactone E or U0126, and then treated with 1 μM of tamoxifen for 1 hour. The cells are then lyzed and protein extracts are prepared for western blot analysis. The membranes are finally incubated in the presence of the various antibodies (p-Erk1/2, Erk1/2 and HSP60). Simalikalactone E and U0126 inhibit Rafl-dependent Erk1/2 (MAP kinase) phosphorylation. These results show that Simalikalactone E blocks the Erk1/2 (MAP kinase) pathway at the level of or upstream of MEK1/2.

B2-4. Xenografts of K562-Luc Cells in Nude Mice

Figure 7:
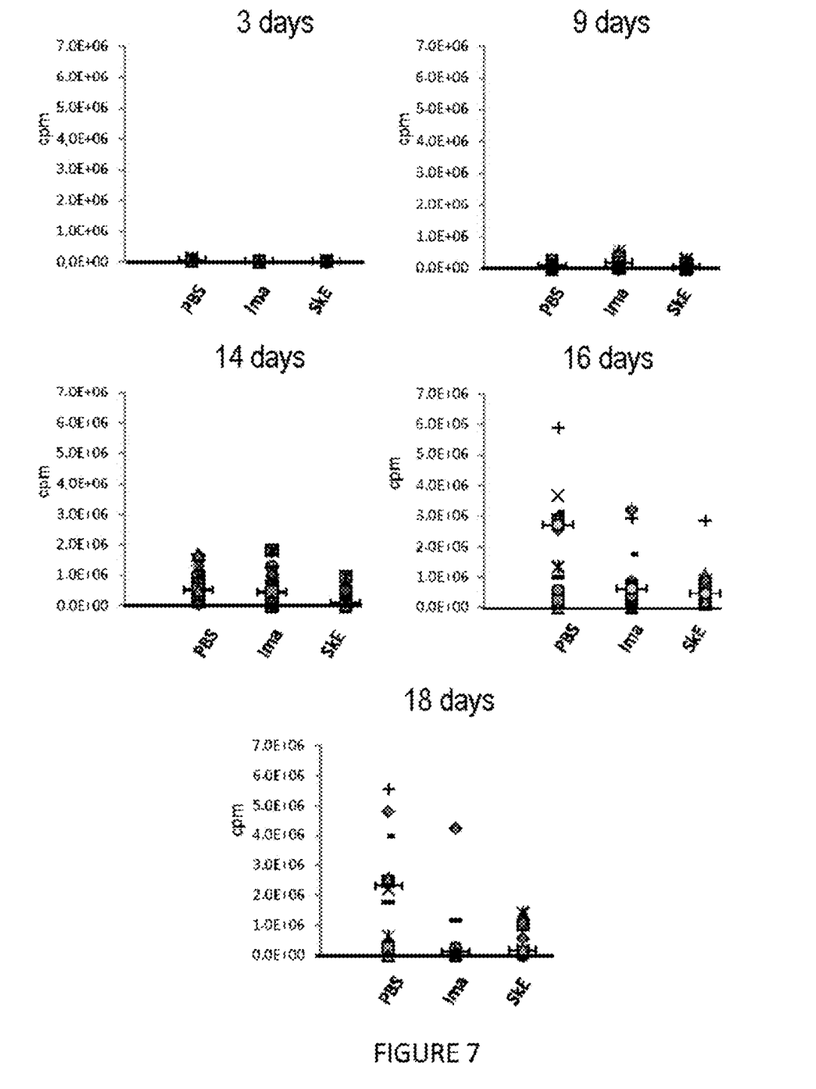
Figure 8:
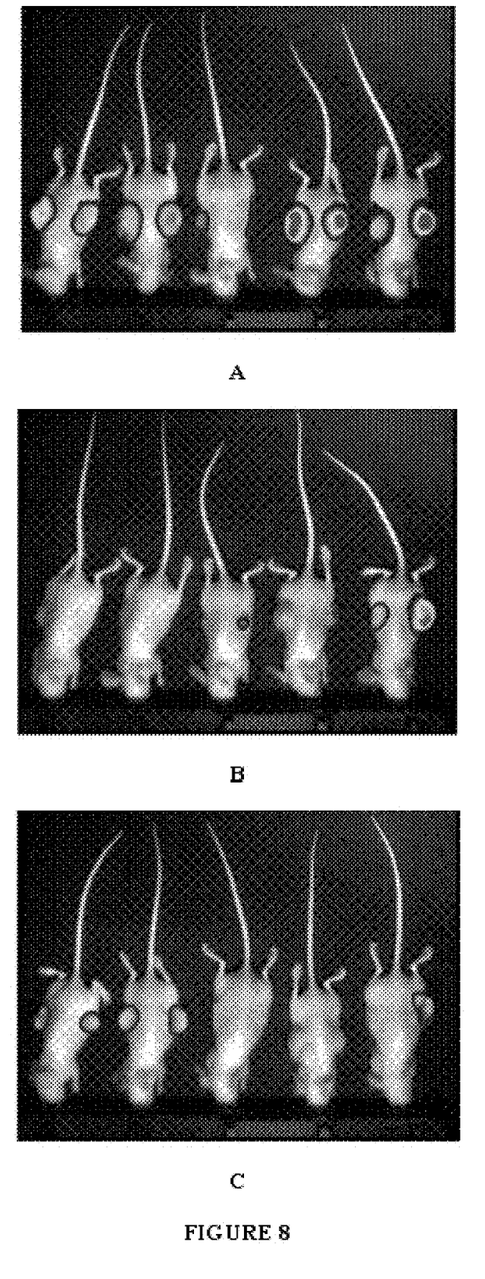

The results of the xenografts of K562-Luc cells on Nude mice are presented in FIGS. 7 and 8.

FIG. 8 shows that the mice treated with PBS (control treatment) exhibit large tumors, in comparison with the mice treated with 60 mg/kg of imatinib (reference treatment) and with the mice treated with 1 mg/kg of SkE.

The invention claimed is:

1. A method of treating cancer in which Ras/Raf/MEK/Erk signaling pathway is activated in a patient comprising a step of administering Simalikalactone E corresponding to formula 1 below:

SkE to the patient in an amount effective to treat said cancer, wherein the Ras/Raf/MEK/Erk signaling pathway is activated in the cancer.

2. The method as claimed in claim 1 wherein the cancer is an epithelial and hematological cancer.

3. The method as claimed in claim 1 wherein the epithelial cancer is chosen from the group consisting of melanoma, breast, prostate, pancreatic, ovarian, kidney, intestinal, colon, lung and thyroid cancers and ear, nose and throat (ENT) cancers.

4. The method as claimed in claim 3, wherein the cancer is melanoma.

5. The method as claimed in claim 1, wherein the cancer is a malignant hemopathy.

6. The method as claimed in claim 5, wherein the malignant hemopathy is chosen from the group consisting of myeloproliferative syndromes (MPS), chronic myeloid leukemia (CML), myelodysplastic syndromes (MDS), multiple myeloma (MM), acute myeloid leukemias (AML) and acute lymphoblastic leukemias (ALL).

7. The method as claimed in claim 6, wherein the malignant hemopathy is chronic myeloid leukemia (CML), myelodysplastic syndromes (MDS), multiple myeloma (MM) or acute lymphoblastic leukemias (ALL).

8. The method as claimed in claim 1, wherein the Simalikalactone E is in a form which is administrable orally, topically, intravenously or subcutaneously.

9. The method as claimed in claim 1, wherein the daily dose of Simalikalactone E administered to the patient ranges from 10 to 50 mg/kg/d.

10. The method as claimed in claim 1, wherein the duration of treatment is between 1 and 60 consecutive days.

11. A pharmaceutical composition, comprising Simalikalactone E corresponding to formula 1 below:

SkE as an active ingredient in combination with another anti-cancer active ingredient, and at least one pharmaceutically acceptable excipient.

12. The pharmaceutical composition as claimed in claim 11, wherein the Simalikalactone E is in a form which is administrable orally, topically, intravenously or subcutaneously.

13. A method of treating a disease caused by activation of Ras/Raf/MEK/Erk signaling pathway in a subject comprising a step of administering Simalikalactone E corresponding to formula 1 below:

SkE to the subject in an amount effective to treat said disease.

14. A method of inhibiting Ras/Raf/MEK/Erk signaling pathway in a subject comprising a step of administering Simalikalactone E corresponding to formula 1 below:

SkE to the subject in an amount effective to inhibit the Ras/Raf/MEK/Erk signaling pathway.

* * * * *